(12) United States Patent
Avegliano et al.

(10) Patent No.: US 10,898,119 B2
(45) Date of Patent: Jan. 26, 2021

(54) COORDINATING ACTIVITIES RESPONSIVE TO PHYSIOLOGIC SIGNALS

(71) Applicant: International Business Machines Corporation, Armonk, NY (US)

(72) Inventors: Priscilla Barreira Avegliano, Sao Paulo (BR); Carlos Henrique Cardonha, Sao Paulo (BR); Lucas Correia Villa Real, Sao Paulo (BR); Juliana de Melo Batista dos Santos, Sao Paulo (BR)

(73) Assignee: International Business Machines Corporation, Armonk, NY (US)

( * ) Notice: Subject to any disclaimer, the term of this patent is extended or adjusted under 35 U.S.C. 154(b) by 334 days.

(21) Appl. No.: 15/988,520

(22) Filed: May 24, 2018

(65) Prior Publication Data

US 2019/0357831 A1    Nov. 28, 2019

(51) Int. Cl.
*A61B 5/00*    (2006.01)
*A61B 5/16*    (2006.01)
(Continued)

(52) U.S. Cl.
CPC ............ *A61B 5/165* (2013.01); *A61B 5/0022* (2013.01); *A61B 5/11* (2013.01); *A61B 5/7225* (2013.01);
(Continued)

(58) Field of Classification Search
CPC ......... A61B 5/11; A61B 5/165; A61B 5/0022; A61B 5/7225; A61B 5/7246;
(Continued)

(56) References Cited

U.S. PATENT DOCUMENTS 4,622,980 A    11/1986    Kunig
4,683,891 A    8/1987    Cornellier et al.
(Continued)

FOREIGN PATENT DOCUMENTS

WO    2006090371 A1    8/2006

OTHER PUBLICATIONS

Peter Mell et al., "The NIST Definition of Cloud Computing". Special Publication 800-145. NIST. Sep. 2011, pp. 1-7.
(Continued)

*Primary Examiner* — Max F Hindenburg
(74) *Attorney, Agent, or Firm* — Joseph Petrokaitis; Otterstedt, Wallace & Kammer, LLP (57) ABSTRACT

A method for coordinating activities includes monitoring physiologic signals and movement signals from a plurality of individuals, and learning at least one baseline for each of the plurality of individuals from the physiologic stress signals and the movement signals. The method further includes comparing the individual's physiologic signals to their baseline, determining a current activity for each individual, and learning correlations between current activities and sequences of activities and estimated divergences of the physiologic signals from baseline. The method also includes determining prospective activities for each individual, identifying at least one prospective shared activity among two or more individuals, estimating prospective divergences of the physiologic signals associated with the prospective shared activity, and mitigating the prospective divergences of the physiologic signals by controlling the scheduling component to adjust a schedule of the at least one prospective shared activity.

20 Claims, 7 Drawing Sheets

(51) Int. Cl.
*G06N 5/04* (2006.01)
*G16H 50/30* (2018.01)
*A61B 5/11* (2006.01)
*G06N 20/00* (2019.01)

(52) U.S. Cl.
CPC .......... *A61B 5/7246* (2013.01); *A61B 5/7267* (2013.01); *A61B 5/7275* (2013.01); *G06N 5/04* (2013.01); *G06N 20/00* (2019.01); *G16H 50/30* (2018.01); *A61B 2503/12* (2013.01)

(58) Field of Classification Search
CPC .... A61B 5/7267; A61B 5/7275; G16H 50/30; G06N 20/00; G06N 99/005; G06N 5/04
See application file for complete search history.

(56) References Cited

U.S. PATENT DOCUMENTS

| | | | |
|---|---|---|---|
| 5,467,268 | A | 11/1995 | Sisley et al. |
| 6,450,820 | B1 | 9/2002 | Palsson et al. |
| 7,228,168 | B2 | 6/2007 | Dardik et al. |
| 8,884,813 | B2 * | 11/2014 | Bangera ............... A61B 5/0507 340/573.1 |
| 9,962,104 | B2 * | 5/2018 | De Vries ............... A61B 5/021 |
| 10,299,715 | B2 * | 5/2019 | Berckmans ............ G16H 50/30 |
| 2003/0154122 | A1 | 8/2003 | Jackson et al. |
| 2007/0277113 | A1 | 11/2007 | Agrawal et al. |
| 2008/0307323 | A1 | 12/2008 | Coffman et al. |
| 2010/0077400 | A1 | 3/2010 | Ioannou |
| 2010/0274100 | A1 | 10/2010 | Behar et al. |
| 2011/0093538 | A1 | 4/2011 | Weir et al. |
| 2011/0125547 | A1 | 5/2011 | Brdiczka et al. |
| 2012/0289788 | A1 * | 11/2012 | Jain .................... G06F 19/3418 600/301 |
| 2014/0058779 | A1 | 2/2014 | Kissoon et al. |
| 2014/0221774 | A1 | 8/2014 | Teller et al. |
| 2015/0302345 | A1 | 10/2015 | Bartlett et al. |
| 2017/0004425 | A1 | 1/2017 | Tomoeda |
| 2017/0243501 | A1 | 8/2017 | Cardonha et al. |
| 2017/0268793 | A1 | 9/2017 | Cardonha et al. |
| 2019/0046107 | A1 * | 2/2019 | Jang .................... A63B 24/0062 |

OTHER PUBLICATIONS

John E. Kelly III, "Computing, cognition, and the future of knowing", IBM Corp. Oct. 2015. pp. 1-7.

Anonymous, "Intelligent prediction of employees' stress levels based on schedule and workload", IP.com IPCOM000235589D. Mar. 2014. pp. 1-2.

Marcos Dias De Assuncao et al., "Impact of User Patience on Auto-Scaling Resource Capacity for Cloud Services". Future Generation Computer Systems, Elsevier, Sep. 2015, pp. 1-13. <hal-01199207>.

Carlos Cardonha et al., "Patience-aware scheduling for cloud services: Freeing users from the chains of boredom", International Conference on Service-Oriented Computing, Aug. 2013, pp. 550-557. arXiv:1308.4166.

Renato L.F. Cunha et al., "Exploiting user patience for scaling resource capacity in cloud services", IEEE 7th International Conference on Cloud Computing, Jun. 2014, pp. 448-455.

Gustavo A. Reyes Del Paso et al., "The utility of low frequency heart rate variability as an index of sympathetic cardiac tone: a review with emphasis on a reanalysis of previous studies", Psychophysiology 50.5. May 2013. pp. 477-487.

Harald M. Stauss. "Heart rate variability". American Journal of Physiology-Regulatory, Integrative and Comparative Physiology 285(5). Nov. 2003. pp. R927-R931.

* cited by examiner

$$\min \sum_{\substack{i \in I \\ m_1, m_2 \in M_i \\ t_1 = t_2 - 1}} c_{m_1, m_2, i} x_{m_1, t_1} x_{m_2, t_2}$$

subject to $$\sum_{t \in T_m} x_{m,t} = 1 \quad \forall m \in M$$

$$\sum_{(m,t) \in M_i \times T_i} x_{m,t} \geq 1 \quad \forall t \in T_i$$

$$x_{m,t} \in \{0, 1\} \quad \forall (m, t) \in M \times T.$$

FIG. 7

US 10,898,119 B2

COORDINATING ACTIVITIES RESPONSIVE TO PHYSIOLOGIC SIGNALS

BACKGROUND

The present invention relates to the electrical, electronic and computer arts, and more specifically, to coordination of computerized calendars among a group.

Computerized calendars have become a common mode of organizing activities. Calendar organization is a challenging task, even at the level of an individual. The challenges faced by individuals include the large number of possibilities that need to be inspected, and the requirement to coordinate with one or more other individuals in situations where their simultaneous participation is desired or required.

SUMMARY

Principles of the invention provide techniques for coordinating activities responsive to stress indicators. In one aspect, an exemplary method includes monitoring physiologic stress signals from a plurality of physiologic sensors, each of the plurality of physiologic sensors corresponding to one of a plurality of individuals composing a group; monitoring movement signals from a plurality of movement sensors, each of the plurality of movement sensors corresponding to one of the plurality of physiologic sensors; learning at least one baseline for each of the plurality of individuals from the physiologic stress signals and the movement signals; estimating a psychological stress level for each of the plurality of individuals by comparing the physiologic stress signals for that individual to the at least one baseline for that individual consistent with the movement signals for that individual; monitoring a scheduling component to determine a current activity for each of the plurality of individuals; learning correlations between current activities and sequences of activities and estimated psychological stress level for each of the plurality of individuals; monitoring the scheduling component to determine prospective activities for each of the plurality of individuals; identifying at least one prospective shared activity among two or more of the plurality of individuals; estimating prospective psychological stress levels associated with the prospective shared activity for each of the two or more individuals, responsive to the learned correlations; and mitigating the prospective psychological stress levels by controlling the scheduling component to adjust a schedule of the at least one prospective shared activity.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a tangible computer readable storage medium (or multiple such media) and implemented on a hardware processor, or (iii) a combination of (i) and (ii); any of (i)-(iii) implement the specific techniques set forth herein.

Thus, aspects of the disclosure provide systems and methods that address certain challenges of group calendar coordination by proposing rearrangements in the calendar of groups of people in a way that all schedules remain feasible and the stress levels of individuals remain at acceptable levels. Modification on stress levels are measured automatically with sensors (e.g., heartbeat, blood pressure, body temperature, basal heart rate, and sleep pattern), so human intervention is kept at a minimum. After the collection of sufficient data, the system is capable of detecting a pattern in the response of a person to a given sequence of events, making the analysis precise. Thus, aspects of the disclosure identify an optimal scheduling of meetings and appointments for a group of individuals enrolled on one or more meetings together. Choices are restricted by time-windows associated with each meeting for each person. The optimization criteria are based on assessment of sensed stress indicators responsive to proposed sequences of meetings and appointments.

In view of the foregoing, techniques of the present invention can provide substantial beneficial technical effects. For example, one or more embodiments provide one or more of:

Automated coordination of group calendars to mitigate individual stress, responsive to sensed stress indicators.

Automated coordination of group calendars to obtain a local minimum of group stress, responsive to sensed stress indicators.

Incorporation of physiologic sensor data into assigning and scheduling tasks and meetings for individuals within a group.

These and other features and advantages of the present invention will become apparent from the following detailed description of illustrative embodiments thereof, which is to be read in connection with the accompanying drawings.

DETAILED DESCRIPTION

According to an exemplary embodiment of the present invention, a measured stress level of an individual may change according to a quality of a sequence of activities, e.g., meetings, potential interactions with other meeting participants, meeting topics, etc. One or more exemplary embodiments of the present invention provide improved event scheduling in the context of an electronically stored calendar, which mitigates prospective psychological stress levels by adjusting a schedule of prospective shared activities. Enhanced productivity and morale and more efficient usage of computing and telecommunications resources can be achieved through the scheduling, which considers arrangements of meetings in an integrated and efficient way by taking into account restrictions and constraints imposed by individuals of a group.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 1:
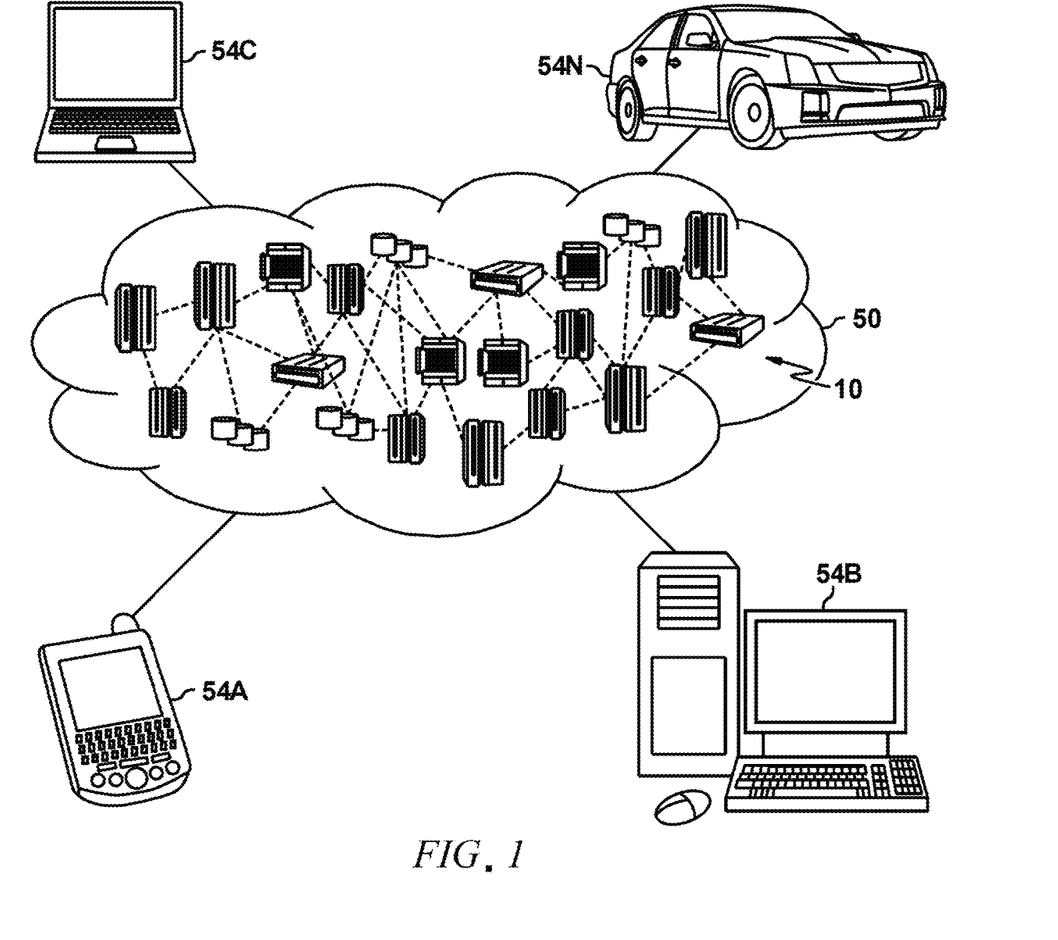
FIG. 1 depicts a cloud computing environment according to an embodiment of the present invention.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
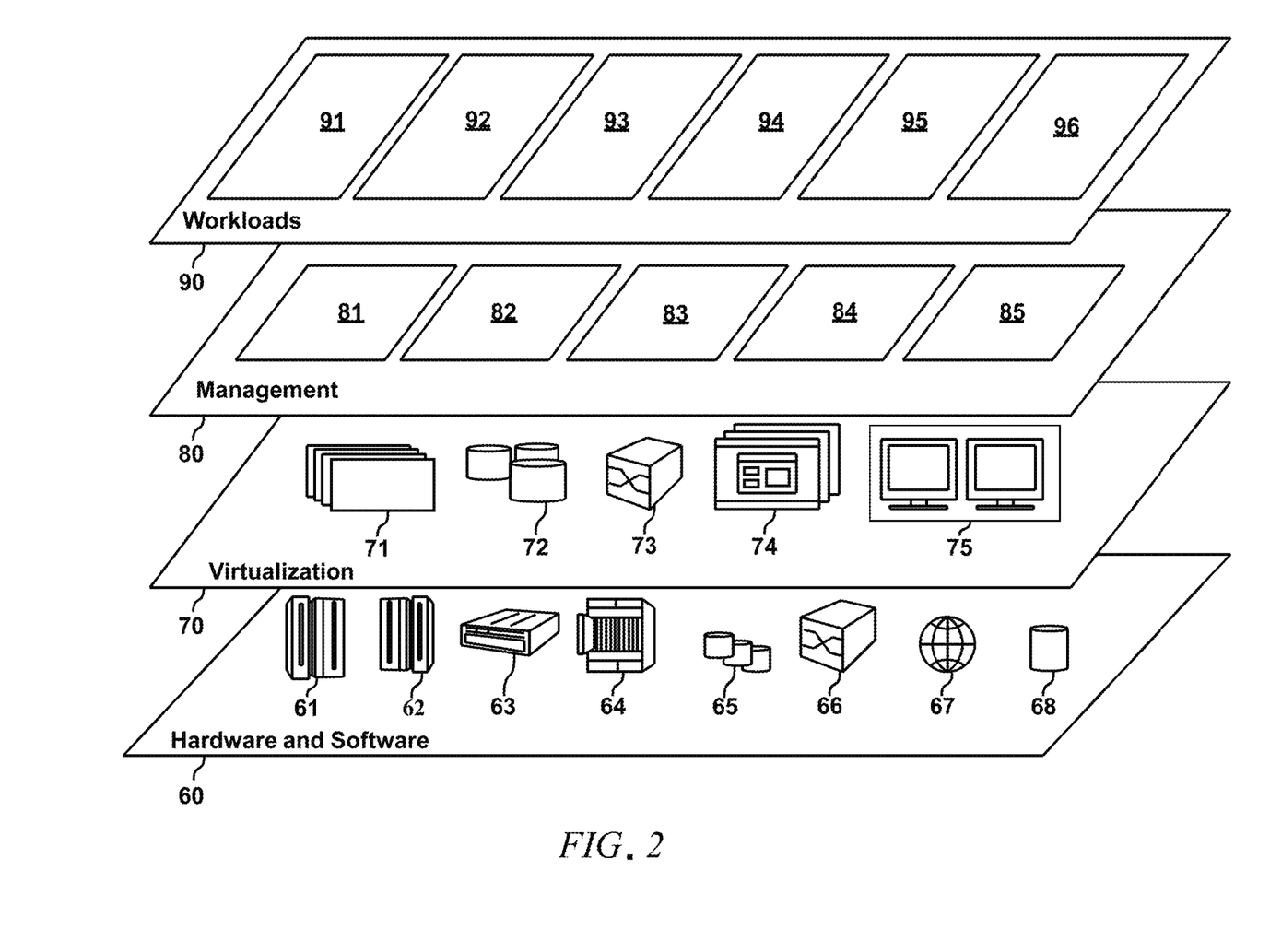
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and a system 96 for coordinating activities responsive to stress indicators.

Figure 3:
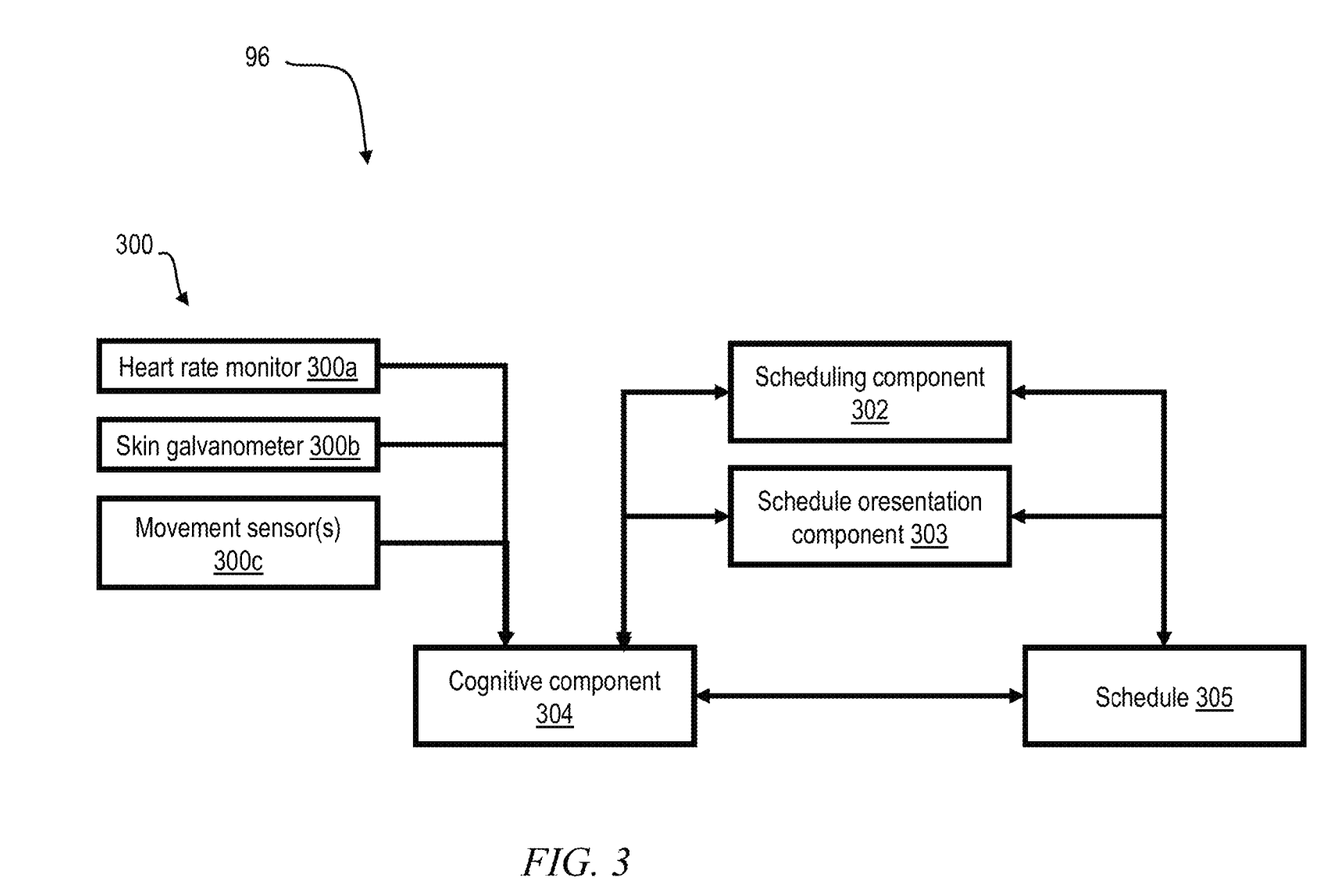
FIG. 3 depicts a system for incorporating stress sensor data into task and meeting assignments and scheduling according to an exemplary embodiment.

Referring to FIG. 3, the system 96 includes a plurality of stress sensors 300a . . . 300n as well as an activity scheduling component 302, a schedule presentation component 303, and a cognitive component 304 that interfaces between the other components.

The sensors 300 include, for example, a heart rate monitor 300a that samples at relatively high frequency, e.g., with a periodicity on the order of milliseconds. In one or more embodiments the sensors 300 also include a skin galvanometer 300b, which also may sample at a relatively high frequency. The sensors 300 also include one or more movement sensors 300c (e.g., accelerometers, motion-sensitive cameras).

The heart rate monitor 300a samples a user's heartbeat to estimate heart rate variability (HRV). HRV is the variation in the time interval between one heartbeat and the next. Emotions and experiences of the external environment are tightly connected to the functioning of nervous system, heart rhythm and breathing. The function of the user's nervous system can be measured, using HRV as an indicator of activity. A person with high levels of HRV experiences low levels of stress and greater resiliency. Low levels of HRV indicate a greater stress and lower resiliency. HRV can be easily monitored using the heart rate monitor 300a with specific software that can translate input from the monitor into HRV levels.

In one or more embodiments, the collected time-series of the HRV is transformed into the frequency domain by applying a Fourier Transformation, for instance (in a Fourier transformation, a periodic signal is decomposed into sin( ) functions of different frequencies). This way, it is possible to classify predominant frequencies (low frequency or high frequency) of the HRV and, consequently, infer the level of stress. The HRV frequency spectrum includes ultra-low frequency related to circadian rhythms (cycle length greater than 5 hours), very low frequency related to thermoregulation and humoral systems (cycle length greater than 25 seconds), low frequency related to cardiac sympathetic nerve activity (cycle length greater than 6 seconds), and high frequency related to cardiac parasympathetic innervation (cycle length 2.5 to 6 seconds). See Harold M. Stauss, "Heart rate variability", American Journal of Physiology Regulatory, Integrative and Comparative Physiology 285 (2003): R927-R931. A study by Gustavo A. Reyes del Paso, et al., "The utility of low frequency heart rate variability as an index of sympathetic cardiac tone: a review with emphasis on a reanalysis of previous studies", Psychophysiology 50.5 (2013): 477-487, suggests that stressful conditions can decrease the peak low frequency oscillation by 0.1 Hertz from its baseline value.

Galvanic skin response (GSR) also known as electrodermal response, psychogalvanic reflex, or skin conductance response, can be used to detect stress through identification of sweat secretion from sweat glands. Skin conductance measured by the skin galvanometer 300b is not under conscious control. It is modulated autonomously by sympathetic activity of nervous system which drives human behavior, cognitive and emotional states on a subconscious level. Increased skin conductance corresponds to stressful conditions.

The cognitive component 304 assesses data from the sensors 300 in order to estimate whether an individual is experiencing psychological stress. To estimate whether stress is physical or psychological, the cognitive component 304 correlates data from the movement sensors 300c to data from the heart rate monitor 300a and the skin galvanometer 300b. In cases where the movement sensors 300c indicate vigorous movement (physical stress), the cognitive component 304 compares the measure HRV and GSR to different baselines than in cases where the movement sensors 300c indicate sedentary or slow movement (minimal physical stress). In one or more embodiments the cognitive component 304 determines the different baselines for different movement conditions by continuously monitoring the HRV, GSR, and user movement.

In one or more embodiments, the cognitive component may include a cognitive neural network. Generally, a cognitive neural network includes a plurality of computer processors that are configured to work together to implement one or more machine learning algorithms. The implementation may be synchronous or asynchronous. In a neural network, the processors simulate thousands or millions of neurons, which are connected by axons and synapses. Each connection is enforcing, inhibitory, or neutral in its effect on the activation state of connected neural units. Each individual neural unit has a summation function which combines the values of all its inputs together. In some implementations, there is a threshold function or limiting function on at least some connections and/or on at least some neural units, such that the signal must surpass the limit before propagating to other neurons. A cognitive neural network can implement supervised, unsupervised, or semi-supervised machine learning.

When the cognitive component 304 estimates psychological stress in a user, it correlates the psychological stress to the user's currently scheduled activity as confirmed by the movement sensors 300c and the scheduling component 302. Over time, the cognitive component 304 learns how scheduled sequences of activities increase or decrease the user's psychological stress. Thus, the cognitive component 304 also correlates the psychological stress to a future activity or sequence of activities (schedule 305) as displayed to the user by the schedule presentation component 303. The cognitive component 304 interacts with the scheduling component 302 to proactively reschedule stressful sequences of activities so as to mitigate the user's psychological stress.

In one or more embodiments, the system 96 is configured to interface with the schedules of multiple individuals who interact in groups (e.g., project teams, softball teams, social clubs). In such embodiments, the cognitive component 304 learns to optimize overall psychological wellness on the task of scheduling common activities. In order to do this, the cognitive component 304 learns how combinations of participants or sequences of common activities affect each individual's prospective psychological stress, based on historic measurements of HRV and GSR during particular activities or participant combinations. In one or more embodiments, the cognitive component 304 also learns from current measurements of HRV and GSR while a prospective schedule is displayed to each individual.

Figure 4:
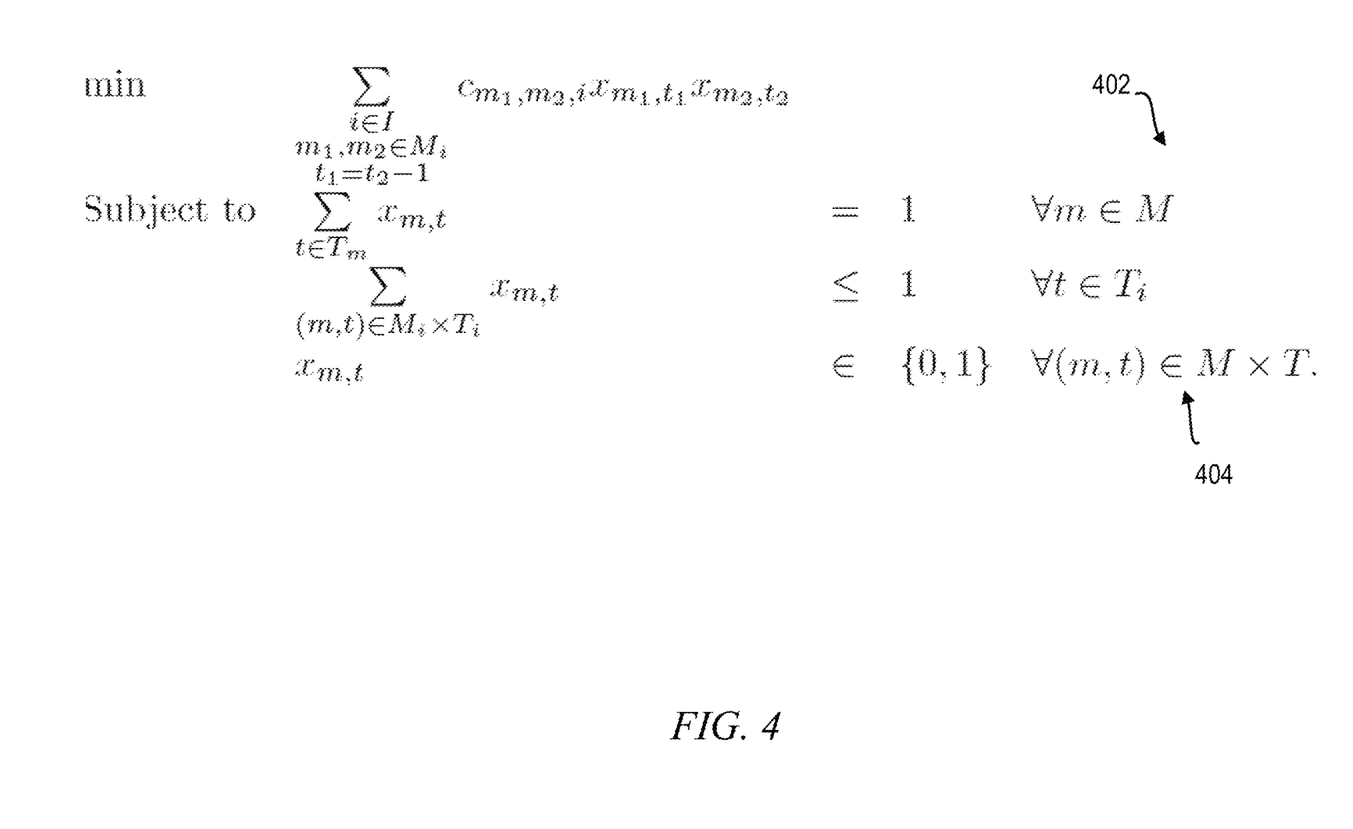
FIG. 4 depicts an optimization algorithm usable with the system of FIG. 3.

According to an exemplary embodiment of the present invention, the cognitive component 304 seeks to optimize psychological wellbeing for each individual and for a group by applying an algorithm 400 as set forth in FIG. 4 and presented here:

$$\min \sum_{\substack{i \in I \\ m_1, m_2 \in M_i \\ t_1 = t_2 - 1}} c_{m_1, m_2, i} x_{m_1, t_1} x_{m_2, t_2}$$

$$\text{Subject to} \quad \sum_{t \in T_m} x_{m,t} = 1 \quad \forall\, m \in M$$

$$\sum_{(m,t) \in M_i \times T_i} x_{m,t} \leq 1 \quad \forall\, t \in T_i$$

$$x_{m,t} \in \{0, 1\} \quad \forall\, (m, t) \in M \times T.$$

Set M represents the meetings and T the time-slots to which meetings are assigned (or scheduled). Set $M_i$ contains the meeting in which individual i is taking part, and set $T_i$ contains the time-slots individual i has available for meetings. Parameters $c_{m1,m2,i}$ associate a cost or penalty to the assignment of meeting $m_1$ to time-slot $t_1$ and meeting $m_2$ to time-slot $t_2 = t_1 + 1$ (i.e., the penalty of having meeting $m_2$ taking place immediately after meeting $m_1$). The first inequality asserts that exactly one time-slot is assigned to each meeting, and the second asserts that at most one meeting is selected per time-slot and per individual. The model aims at the minimization of the penalties (in terms of psychological stress, as measured/learned from HRV and GSR sensors 300a, 300b) that could be incurred due to pairs of successive meetings.

In one or more embodiments, the algorithm 400 is non-linear so that the cognitive component 304 needs to apply techniques such as constraint programming to solve it. Constraint programming technology is used to find solutions to scheduling and combinatorial optimization problems. It is based primarily on computer science fundamentals, such as logic programming and graph theory, in contrast to mathematical programming, which is based on numerical linear algebra.

In one or more embodiments the algorithm 400 is linearized to permit the use of integer programming methods to solve.

Figure 5:
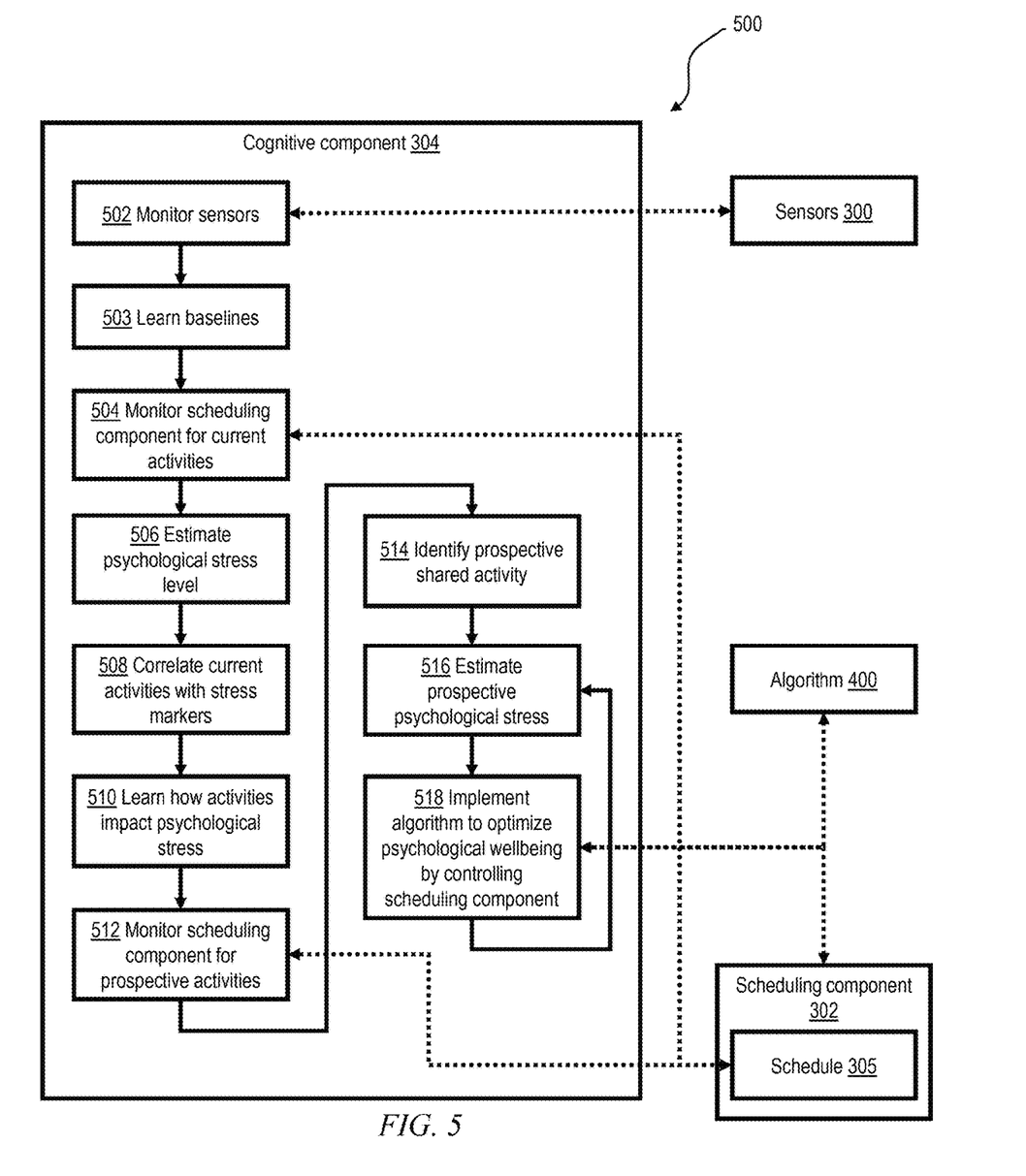
FIG. 5 depicts a method for incorporating stress sensor data into task and meeting assignments and scheduling according to an exemplary embodiment.

Thus, the system 96 implements a method 500 as depicted in FIG. 5. At 502, the cognitive component 304 monitors the physiologic sensor 300a, 300b for signals of stress and monitors the movement sensors 300c for signals of physical activity. At 503, the cognitive component 304 learns baselines of stress signals for multiple movement conditions, including at least a sedentary condition and an active condition. For example, the cognitive component 304 learns the baselines by averaging historic daily minimum values for each condition, eventually removing outliers in order to avoid the influence of extreme scenarios (e.g., extremely low measurements due to sensor failure or very high measurements, which indicate already stressing situations). At 504, the cognitive component 304 monitors the scheduling component 302 to detect current activities for each individual. At 506, the cognitive component 304 estimates a psychological stress level by monitoring the physiologic sensors 300a, 300b and comparing their signals to the baseline for the movement condition indicated by the movement sensors 300c. At 508, the cognitive component 304 correlates current activities with physiologic markers of psychological stress. At 510, the cognitive component 304 learns what current activities and prospective activities enhance or mitigate psychological stress for each individual. At 512, the cognitive component 304 monitors the scheduling component 302 to determine prospective activities for each of the plurality of individuals. At 514, the cognitive component 304 identifies at least one prospective shared activity among two or more of the plurality of individuals. At 516, the cognitive component 304 estimates prospective psychological stress levels associated with the prospective shared activity for each of the two or more individuals, responsive to the learned correlations. At 518, the cognitive component 304 implements the algorithm 400 to optimize psychological wellbeing of a group of individuals by controlling the scheduling component 302 to adjust the schedule 305 of the at least one prospective shared activity.

Figure 6:
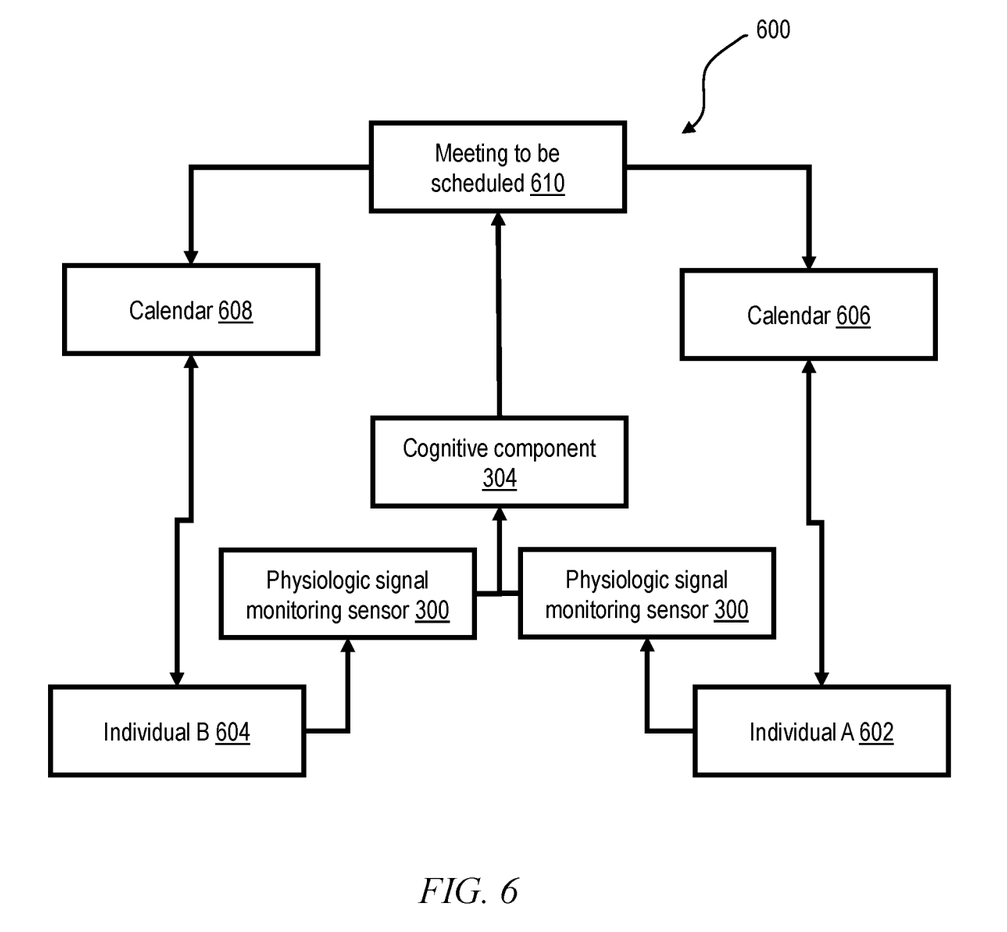
FIG. 6 depicts a globally optimized calendar reallocation according to an exemplary embodiment.

Referring to FIG. 6, the system 96 automatically generates a globally optimized calendar reallocation 600 to accommodate individual and collective activities that optimize the psychological wellbeing of all participants in a group. The system 96 uses the sensors 300 to monitor physiologic and psychological stress and uses the cognitive component 304 to predict psychological stress for several individuals 602, 604 and to adjust their schedules 606, 608 in order to coordinate one or more group activities 610, taking into account what is feasible for everyone in the group. Thus, one or more embodiments focus on rearranging meetings in a way that the meetings become feasible for all stakeholders and their stress levels are reduced. In other words, embodiments attempt to avoid situations where the workforce actually becomes stressed, with the support of sensing technology (to capture honest signals indicating stress levels) combined with the optimization algorithm of FIG. 4, which optimizes the scheduling for the whole group of individuals.

Notably, in one or more embodiments the cognitive component 304 applies natural language processing (NLP) to infer the meaning or context of past, present, and future scheduled tasks (e.g., financial matters, managing activities). By correlating measured psychological stress of a past or present task with future tasks that are assessed to have the same meaning or context (even if not identically described), it becomes possible to intelligently infer the prospective stress level of a scheduled activity even in case the user has not previously performed the very particular task.

In one or more embodiments, the cognitive component 304 has learned not only what activities induce elevated psychological stress in users, but also what combinations of activity participants induce psychological stress. Accordingly, in such embodiments the cognitive component 304 assesses the invitee status of each participant (e.g., required participants cannot be changed, optional ones may be included or removed by the system) and identifies and removes optional participants whose presence has been learned to induce psychological stress in a certain number of required participants.

Given the discussion thus far, it will be appreciated that, in general terms, an exemplary method 500, according to an aspect of the invention, includes 502 monitoring physiologic stress signals from a plurality of physiologic sensors 300a, 300b, each of the plurality of physiologic sensors corresponding to one of a plurality of individuals composing a group and monitoring movement signals from a plurality of movement sensors 300c, each of the plurality of movement sensors corresponding to one of the plurality of physiologic sensors; 503 learning at least one baseline for each of the plurality of individuals from the physiologic stress signals and the movement signals; 506 estimating a psychological stress level for each of the plurality of individuals by comparing the physiologic stress signals for that individual to the at least one baseline for that individual consistent with the movement signals for that individual; 504 monitoring a scheduling component to determine a current activity for each of the plurality of individuals; 508, 510 learning correlations between current activities and sequences of activities and estimated psychological stress level for each of the plurality of individuals; 512 monitoring the scheduling component to determine prospective activities for each of the plurality of individuals; 514 identifying at least one prospective shared activity among two or more of the plurality of individuals; 516 estimating prospective psychological stress levels associated with the prospective shared activity for each of the two or more individuals, responsive to the learned correlations; and 518 mitigating the prospective psychological stress levels by controlling the scheduling component to adjust a schedule of the at least one prospective shared activity. In one or more embodiments, estimating prospective psychological stress levels includes identifying common context among the prospective shared activity and at least one of the current activities by applying natural language processing to a descriptor of the prospective shared activity and to descriptors of the current activities. In one or more embodiments, the current activity is defined by factors including a task and participants in the task. In one or more embodiments, controlling the scheduling component includes changing a scheduled time of the prospective shared activity. In one or more embodiments, controlling the scheduling component includes changing a list of participants in the prospective shared activity. In one or more embodiments, changing the list of participants includes removing an optional participant from the list. In one or more embodiments, mitigating the prospective psychological stress levels is done according to an optimization algorithm such as the optimization algorithm 400.

Figure 7:
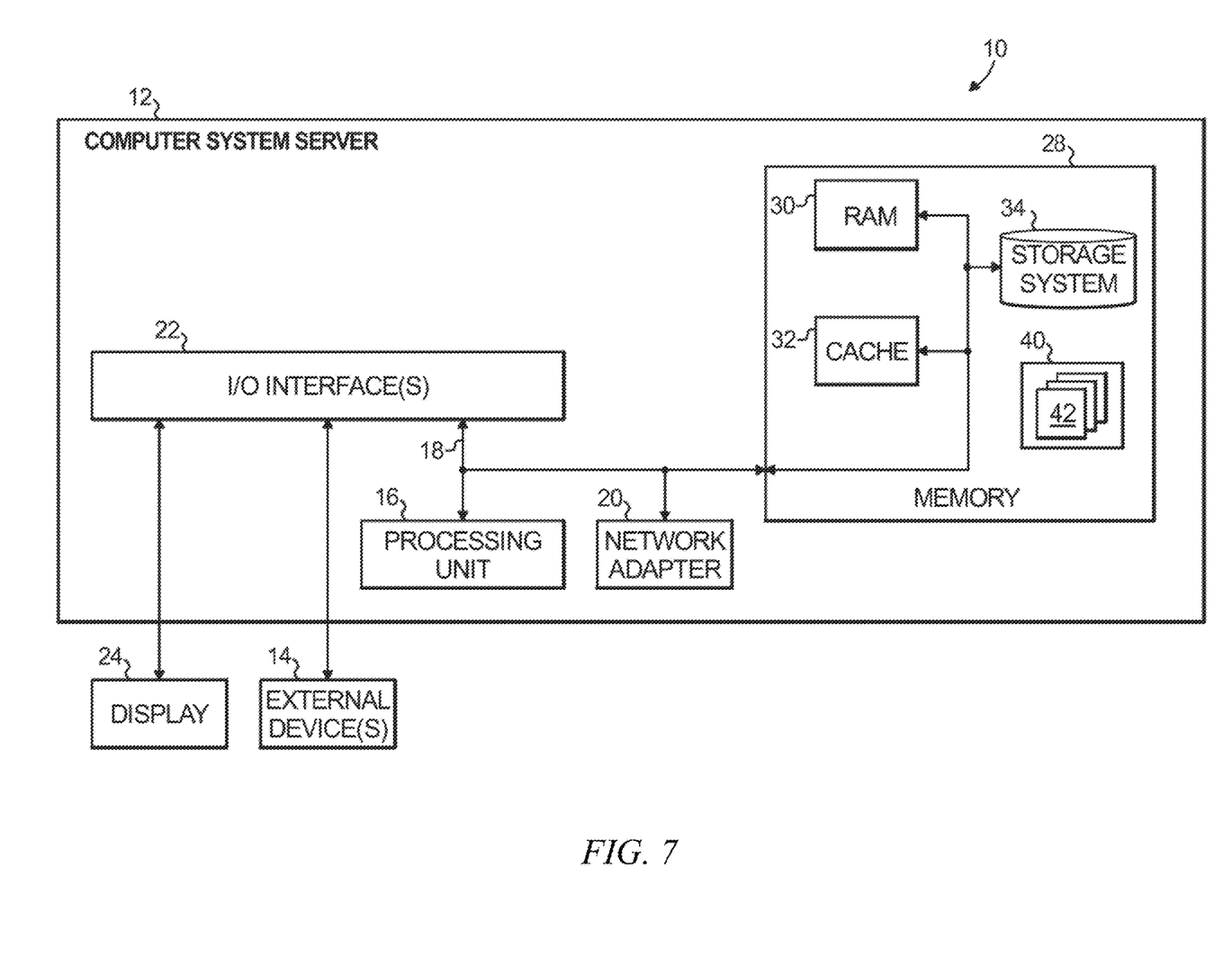
FIG. 7 depicts a computer system that may be useful in implementing one or more aspects and/or elements of the invention, also representative of a cloud computing node according to an embodiment of the present invention.

One or more embodiments of the invention, or elements thereof, can be implemented in the form of an apparatus including a memory and at least one processor that is coupled to the memory and operative to perform exemplary method steps, or in the form of a non-transitory computer readable medium embodying computer executable instructions which when executed by a computer cause the computer to perform exemplary method steps. FIG. 7 depicts a computer system that may be useful in implementing one or more aspects and/or elements of the invention, also representative of a cloud computing node according to an embodiment of the present invention. Referring now to FIG. 7, cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Thus, one or more embodiments can make use of software running on a general purpose computer or workstation. With reference to FIG. 7, such an implementation might employ, for example, a processor 16, a memory 28, and an input/output interface 22 to a display 24 and external device(s) 14 such as a keyboard, a pointing device, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 7) running a server program. It will be understood that such a physical server may or may not include a display and keyboard.

One or more embodiments can be at least partially implemented in the context of a cloud or virtual machine environment, although this is exemplary and non-limiting. Reference is made back to FIGS. 1-2 and accompanying text.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules.

One example of user interface that could be employed in some cases is hypertext markup language (HTML) code served out by a server or the like, to a browser of a computing device of a user. The HTML is parsed by the browser on the user's computing device to create a graphical user interface (GUI).

Exemplary System and Article of Manufacture Details

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for mitigating prospective psychological stress levels, the method comprising:
    monitoring physiologic stress signals from a plurality of physiologic sensors, each of the plurality of physiologic sensors corresponding to one of a plurality of individuals composing a group;
    monitoring movement signals from a plurality of movement sensors, each of the plurality of movement sensors corresponding to one of the plurality of physiologic sensors;
    learning at least one baseline for each of the plurality of individuals from the physiologic stress signals and the movement signals;
    estimating a psychological stress level for each of the plurality of individuals by comparing the physiologic stress signals for that individual to the at least one baseline for that individual consistent with the movement signals for that individual;
    monitoring a scheduling component to determine a current activity for each of the plurality of individuals;
    learning correlations between current activities and sequences of activities and estimated psychological stress level for each of the plurality of individuals;
    monitoring the scheduling component to determine prospective activities for each of the plurality of individuals;
    identifying at least one prospective shared activity among two or more of the plurality of individuals;
    estimating prospective psychological stress levels associated with the prospective shared activity for each of the two or more individuals, responsive to the learned correlations; and
    mitigating the prospective psychological stress levels by controlling the scheduling component to adjust a schedule of the at least one prospective shared activity.

2. The method of claim 1 wherein estimating prospective psychological stress levels includes identifying common context among the prospective shared activity and at least one of the current activities by applying natural language processing to a descriptor of the prospective shared activity and to descriptors of the current activities.

3. The method of claim 1 wherein the current activity is defined by factors including a task and participants in the task.

4. The method of claim 1 wherein controlling the scheduling component includes changing a scheduled time of the prospective shared activity.

5. The method of claim 1 wherein controlling the scheduling component includes changing a list of participants in the prospective shared activity.

6. The method of claim 5 wherein changing the list of participants includes removing an optional participant from the list.

7. The method of claim 1 wherein mitigating the prospective psychological stress levels is done according to an optimization algorithm $$\min \sum_{\substack{i \in I \\ m_1, m_2 \in M_i \\ t_1 = t_2 - 1}} c_{m_1, m_2, i} x_{m_1, t_1} x_{m_2, t_2}$$

$$\text{Subject to} \sum_{t \in T_m} x_{m,t} = 1 \quad \forall\, m \in M$$

$$\sum_{(m,t) \in M_i \times T_i} x_{m,t} \leq 1 \quad \forall\, t \in T_i$$

$$x_{m,t} \in \{0, 1\} \quad \forall\, (m, t) \in M \times T,$$

where set M represents the plurality of prospective shared activities, set T represents a plurality of time-slots available for scheduling the plurality of prospective shared activities, set $M_i$ contains the meeting in which individual i is taking part, set $T_i$ contains the time-slots individual i has available for meetings, and parameters $c_{m1,m2,i}$ associate a value of psychological stress with an assignment of meeting mi to time-slot $t_1$ and meeting $m_2$ to time-slot $t_2 = t_1 + 1$.

8. An apparatus for mitigating prospective psychological stress levels, the apparatus comprising:
    a plurality of physiologic sensors each corresponding to one of a plurality of individuals composing a group, and each producing a physiologic stress signal;
    a plurality of movement sensors each corresponding to one of the plurality of physiologic sensors, and each producing a movement signal;
    a scheduling component implemented by a processor and producing a plurality of schedules each corresponding to one of the plurality of individuals; and
    a cognitive component implemented by the processor or by another processor and connected in communication with the plurality of physiologic sensors, the plurality of movement sensors, and the scheduling component, wherein the cognitive component facilitates:
        monitoring the physiologic stress signals from the plurality of physiologic sensors;
        monitoring the movement signals from the plurality of movement sensors;
        learning at least one baseline for each of the plurality of individuals from the physiologic stress signals and the movement signals;
        estimating a psychological stress level for each of the plurality of individuals by comparing the physiologic stress signals for that individual to the at least one baseline for that individual consistent with the movement signals for that individual;
        monitoring the scheduling component to determine a current activity for each of the plurality of individuals;
        learning correlations between current activities and sequences of activities and estimated psychological stress level for each of the plurality of individuals;
        monitoring the scheduling component to determine prospective activities for each of the plurality of individuals;

identifying at least one prospective shared activity among two or more of the plurality of individuals;

estimating prospective psychological stress levels associated with the prospective shared activity for each of the two or more individuals, responsive to the learned correlations; and mitigating the prospective psychological stress levels by controlling the scheduling component to adjust a schedule of the at least one prospective shared activity.

9. The apparatus of claim 8 wherein estimating prospective psychological stress levels includes identifying common context among the prospective shared activity and at least one of the current activities by applying natural language processing to a descriptor of the prospective shared activity and to descriptors of the current activities.

10. The apparatus of claim 8 wherein the current activity is defined by factors including a task and participants in the task.

11. The apparatus of claim 8 wherein controlling the scheduling component includes changing a scheduled time of the prospective shared activity.

12. The apparatus of claim 8 wherein controlling the scheduling component includes changing a list of participants in the prospective shared activity.

13. The apparatus of claim 12 wherein changing the list of participants includes removing an optional participant from the list.

14. The apparatus of claim 8 wherein mitigating the prospective psychological stress levels is done according to an optimization algorithm $$\min \sum_{\substack{i \in I \\ m_1, m_2 \in M_i \\ t_1 = t_2 - 1}} c_{m_1, m_2, i} x_{m_1, t_1} x_{m_2, t_2}$$

$$\text{Subject to} \quad \sum_{t \in T_m} x_{m,t} = 1 \quad \forall m \in M$$

$$\sum_{(m,t) \in M_i \times T_i} x_{m,t} \leq 1 \quad \forall t \in T_i$$

$$x_{m,t} \in \{0, 1\} \quad \forall (m, t) \in M \times T,$$

where set M represents the plurality of prospective shared activities, set T represents a plurality of time-slots available for scheduling the plurality of prospective shared activities, set $M_i$ contains the meeting in which individual i is taking part, set $T_i$ contains the time-slots individual i has available for meetings, and parameters associate a value of psychological stress with an assignment of meeting mi to time-slot $t_1$ and meeting $m_2$ to time-slot $t_2 = t_1 + 1$.

15. A non-transitory computer readable medium embodying computer executable instructions for mitigating prospective psychological stress levels, which when executed by a computer processor cause the computer processor to facilitate:

monitoring physiologic stress signals from a plurality of physiologic sensors, each of the plurality of physiologic sensors corresponding to one of a plurality of individuals composing a group;

monitoring movement signals from a plurality of movement sensors, each of the plurality of movement sensors corresponding to one of the plurality of physiologic sensors;

learning at least one baseline for each of the plurality of individuals from the physiologic stress signals and the movement signals;

estimating a psychological stress level for each of the plurality of individuals by comparing the physiologic stress signals for that individual to the at least one baseline for that individual consistent with the movement signals for that individual;

monitoring a scheduling component to determine a current activity for each of the plurality of individuals;

learning correlations between current activities and sequences of activities and estimated psychological stress level for each of the plurality of individuals;

monitoring the scheduling component to determine prospective activities for each of the plurality of individuals;

identifying at least one prospective shared activity among two or more of the plurality of individuals;

estimating prospective psychological stress levels associated with the prospective shared activity for each of the two or more individuals, responsive to the learned correlations; and mitigating the prospective psychological stress levels by controlling the scheduling component to adjust a schedule of the at least one prospective shared activity.

16. The computer readable medium of claim 15 wherein estimating prospective psychological stress levels includes identifying common context among the prospective shared activity and at least one of the current activities by applying natural language processing to a descriptor of the prospective shared activity and to descriptors of the current activities.

17. The computer readable medium of claim 15 wherein the current activity is defined by factors including a task and participants in the task.

18. The computer readable medium of claim 15 wherein controlling the scheduling component includes changing a scheduled time of the prospective shared activity.

19. The computer readable medium of claim 15 wherein controlling the scheduling component includes changing a list of participants in the prospective shared activity.

20. The computer readable medium of claim 15 wherein mitigating the prospective psychological stress levels is done according to an optimization algorithm $$\min \sum_{\substack{i \in I \\ m_1, m_2 \in M_i \\ t_1 = t_2 - 1}} c_{m_1, m_2, i} x_{m_1, t_1} x_{m_2, t_2}$$

$$\text{Subject to} \quad \sum_{t \in T_m} x_{m,t} = 1 \quad \forall m \in M$$

$$\sum_{(m,t) \in M_i \times T_i} x_{m,t} \leq 1 \quad \forall t \in T_i$$

$$x_{m,t} \in \{0, 1\} \quad \forall (m, t) \in M \times T,$$

where set M represents the plurality of prospective shared activities, set T represents a plurality of time-slots available for scheduling the plurality of prospective shared activities, set $M_i$ contains the meeting in which individual i is taking part, set $T_i$ contains the time-slots individual i has available for meetings, and parameters associate a value of psychological stress with an assignment of meeting mi to time-slot $t_1$ and meeting $m_2$ to time-slot $t_2 = t_1 + 1$.

* * * * *